US008674112B2

(12) United States Patent
Bauer et al.

(10) Patent No.: US 8,674,112 B2
(45) Date of Patent: *Mar. 18, 2014

(54) POLYMORPH OF A PHARMACEUTICAL

(75) Inventors: John F. Bauer, Lake Bluff, IL (US);
Azita Saleki-Gerhardt, Libertyville, IL (US); Bikshandarkoil A. Narayanan, Newton, CT (US); Sanjay R. Chemburkar, Gurnee, IL (US); Ketan M. Patel, Wheeling, IL (US); Harry O. Spiwek, Kenosha, WI (US); Philip E. Bauer, Chester Springs, PA (US); Kimberly A. Allen, Trevor, WI (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/480,882

(22) Filed: May 25, 2012

(65) Prior Publication Data

US 2012/0232284 A1    Sep. 13, 2012

Related U.S. Application Data

(60) Continuation of application No. 12/644,439, filed on Dec. 22, 2009, now Pat. No. 8,193,367, which is a continuation of application No. 11/524,972, filed on Sep. 21, 2006, now Pat. No. 7,659,405, which is a continuation of application No. 10/901,818, filed on Jul. 29, 2004, now Pat. No. 7,183,416, which is a division of application No. 09/356,736, filed on Jul. 19, 1999, now Pat. No. 6,894,171.

(60) Provisional application No. 60/093,432, filed on Jul. 20, 1998, provisional application No. 60/137,535, filed on Jun. 4, 1999.

(51) Int. Cl.
*C07D 417/12*    (2006.01)

(52) U.S. Cl.
USPC .......................................................... 548/204

(58) Field of Classification Search
USPC .......................................................... 548/204
See application file for complete search history.

(56) References Cited

U.S. PATENT DOCUMENTS

| | | | |
|---|---|---|---|
| 5,484,801 A | 1/1996 | Al-Razzak et al. | |
| 5,541,206 A * | 7/1996 | Kempf et al. | 514/365 |
| 5,559,158 A | 9/1996 | Al-Razzak et al. | |
| 5,567,823 A | 10/1996 | Tien et al. | |
| 5,635,523 A | 6/1997 | Kempf et al. | |
| 5,648,497 A | 7/1997 | Kempf et al. | |
| 5,674,882 A | 10/1997 | Kempf et al. | |
| 5,725,878 A | 3/1998 | Al-Razzak et al. | |
| 6,894,171 B1 | 5/2005 | Bauer et al. | |
| 7,148,359 B2 | 12/2006 | Chemburkar et al. | |
| 7,183,416 B2 | 2/2007 | Chemburkar et al. | |
| 7,659,405 B2 * | 2/2010 | Bauer et al. | 548/204 |
| 8,193,367 B2 * | 6/2012 | Bauer et al. | 548/204 |

FOREIGN PATENT DOCUMENTS

| | | |
|---|---|---|
| EP | 1097148 A2 | 5/2001 |
| EP | 1418174 B1 | 3/2009 |
| WO | 9414436 A1 | 7/1994 |
| WO | 9509614 A1 | 4/1995 |
| WO | 9639398 A1 | 12/1996 |
| WO | 9701349 A1 | 1/1997 |
| WO | 9822106 A1 | 5/1998 |

OTHER PUBLICATIONS

Baber N., et al., "Clinical trials and good clinical practice" in: The Textbook of Pharmaceutical Medicine, Fourth Edition, BMJ Books London, 2002, pp. 283.
Bauer J., et al., "Ritonavir: An Extraordinary Example of Conformational Polymorphism," 2001, vol. 18 (6), pp. 859-866.
Byrn S., et al., "Pharmaceutical Solids: A Strategic Approach to Regulatory Considerations," 1995, vol. 12 (7), pp. 945-954.
Byrn S.R., et al., "Solid-State Pharmaceutical Chemistry," Chem. Mater., 1994, vol. 6, pp. 1148-1158.
Byrn S.R., "Solid-State Chemistry of Drugs" Academic Press, 1982, pp. 3-27 and 79-148.
Caira M.R., "Crystalline Polymorphism Of Organic Compounds," 1998, vol. 198, pp. 163-208.
Cheronis N. D., "Purification of Solids by Crystallization" in: Semimicro Experimental Organic Chemistry, Chapter 5, John de Graff, Inc., 1958, pp. 31-49.
CIPLA Opposition, Oct. 29, 2010, CIPLA.
Dunitz J.D., et al., "Disappearing Polymorphs," Accounts of Chemical Research, 1995, vol. 28, pp. 193-200.
European Search Report for Application No. EP03029709, mailed on Feb. 24, 2003, 15 pages.
European Search Report for Application No. EP08007622, mailed on Dec. 1, 2008, 9 pages.
INP/DNP Opposition dated Aug. 31, 2006.
Opposition Filed by Matrix Laboratories on Indian Application No. 676/MUMNP/2007 dated Apr. 28, 2011.
Opposition Filed by Matrix Laboratories on Indian Application No. 677/MUMNP/2007 dated Apr. 28, 2011.
Opposition Filed by Matrix Laboratories on Indian Application No. 1638 /MUMNP/2007 dated Apr. 28, 2011.
Ranbaxy Opposition dated Jul. 11, 2005.

* cited by examiner

*Primary Examiner* — Laura L. Stockton
(74) *Attorney, Agent, or Firm* — Michael J. Ward

(57) ABSTRACT

A new crystalline polymorph of ritonavir and methods for its use and preparation are disclosed.

6 Claims, 10 Drawing Sheets

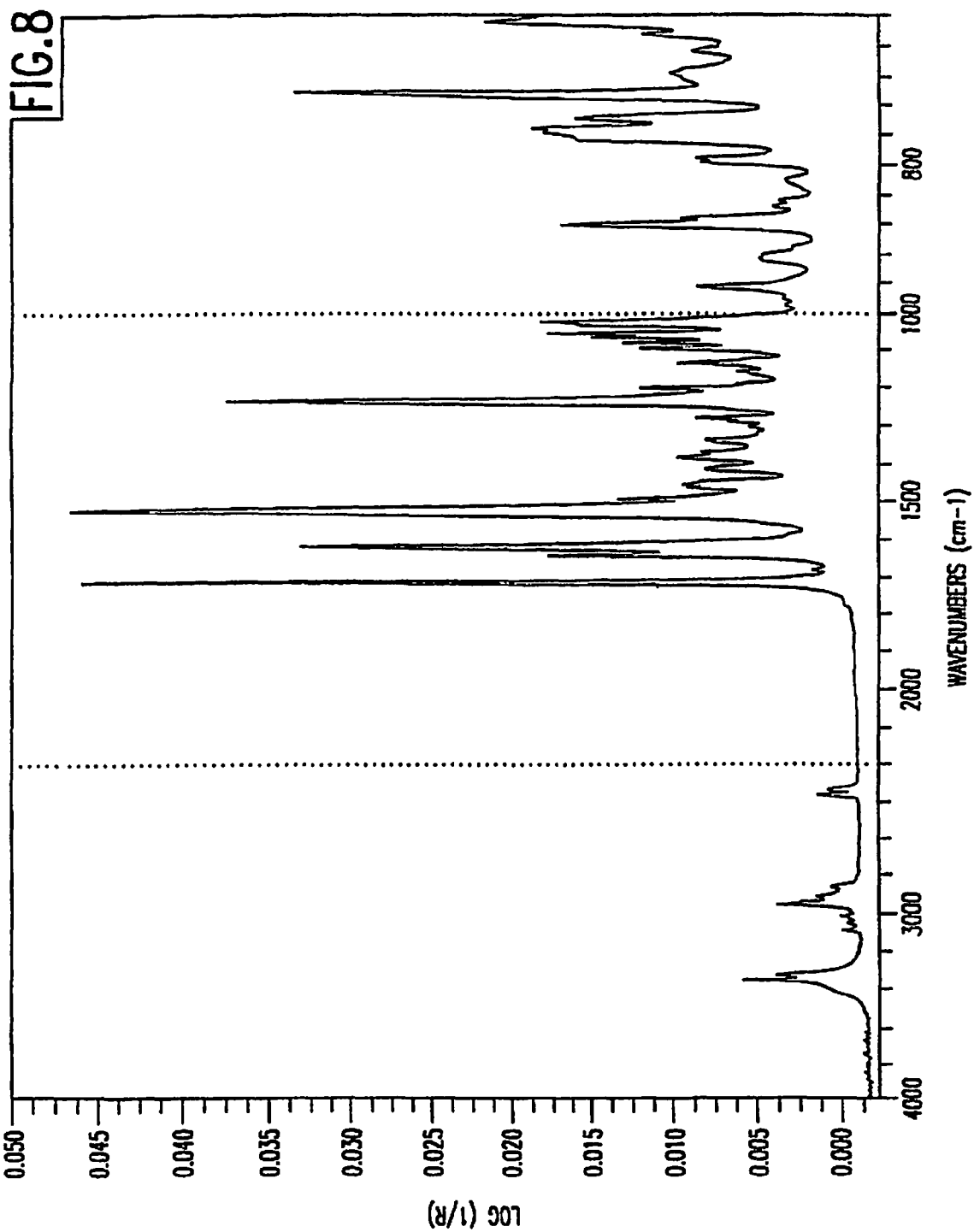

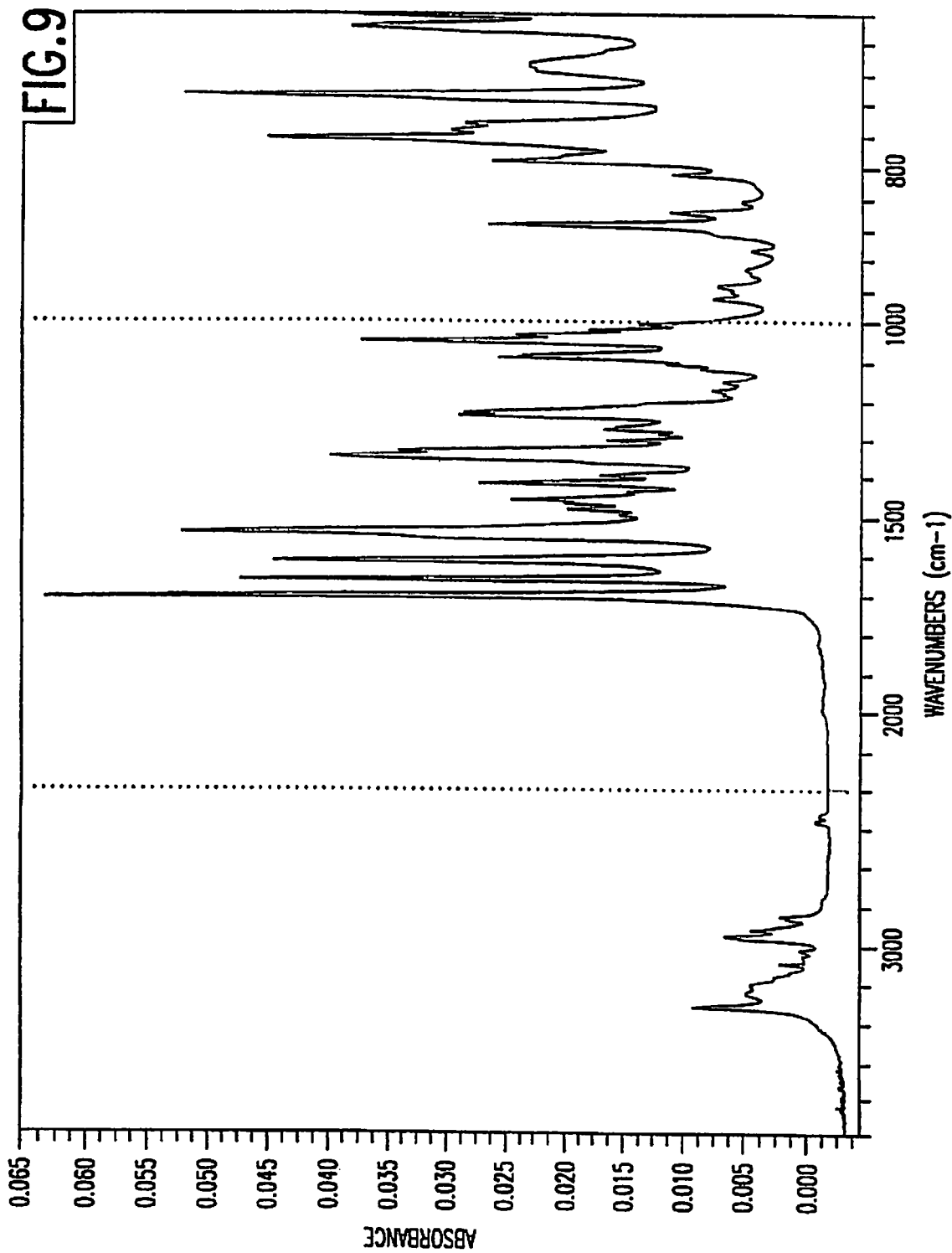

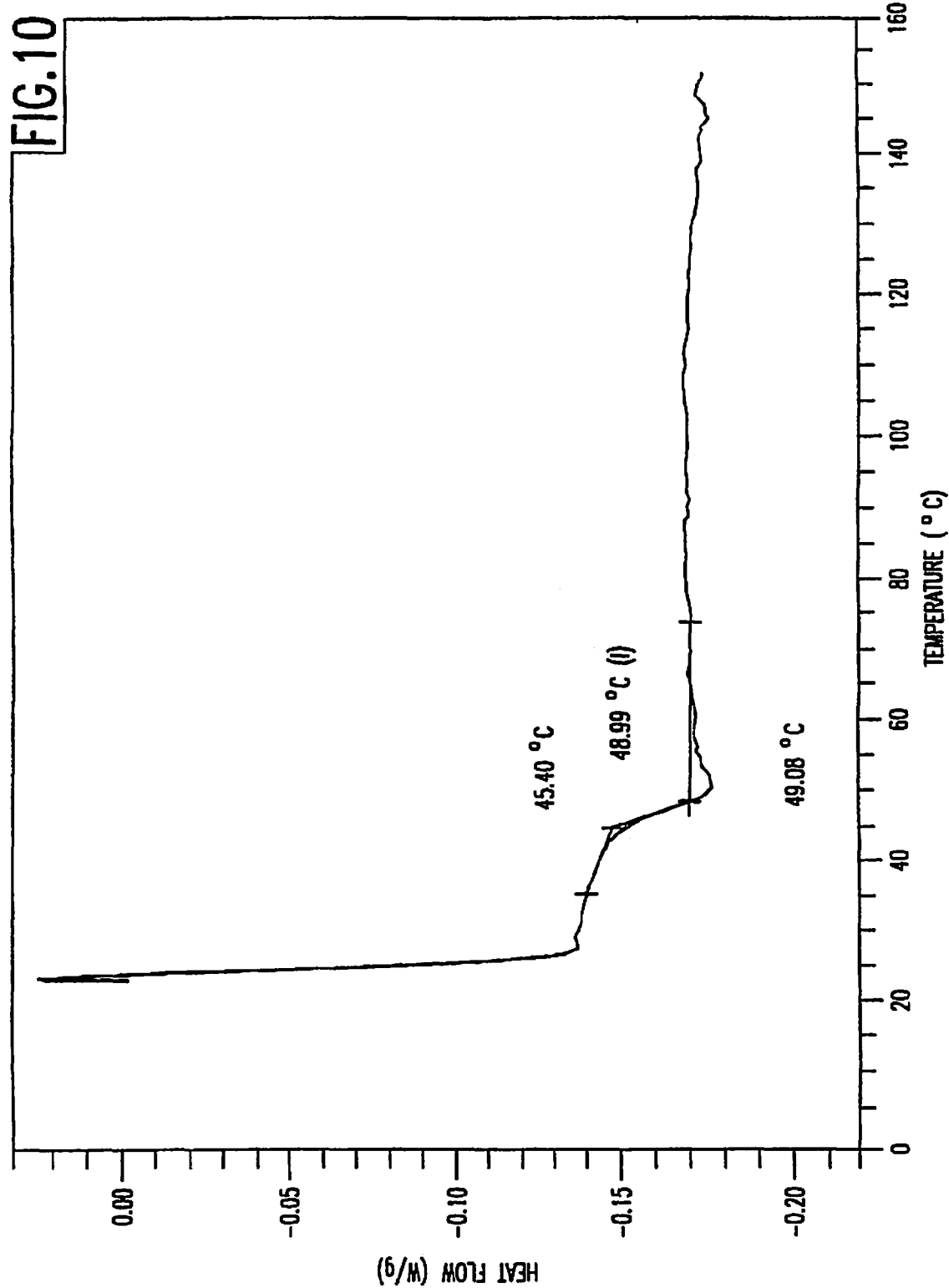

POLYMORPH OF A PHARMACEUTICAL

This application is a continuation of U.S. patent application Ser.No. 12/644,439, filed on Dec. 22, 2009, now U.S. Pat. No. 8,193,367, which is a continuation of U.S. patent application Ser. No. 11/524,972, filed on Sep. 21, 2006, now U.S. Pat. No. 7,659,405, which is a continuation of U.S. patent application Ser. No. 10/901,818, filed on Jul. 29, 2004, now U.S. Pat. No. 7,183,416, which is a divisional of 09/356,736, filed on Jul. 19, 1999, now U.S. Pat. No. 6,894,171, which claims the benefit of U.S. Provisional Application No. 60/093,432, filed on Jul. 20, 1998, and U.S. Provisional Application No. 60/137,535, filed on Jun. 4, 1999.

TECHNICAL FIELD

This invention relates to a novel crystalline polymorph of (2S,3S,5S)-5-(N-(N-((N-methyl-N-((2-isopropyl-4-thiazolyl)methyl)amino)carbonyl)-L-valinyl)amino)-2-(N-((5-thiazolyl)methoxycarbonyl)amino)-1,6-diphenyl-3-hydroxyhexane, methods for its preparation, methods for its use as a pharmaceutical agent and pharmaceutical compositions comprising the novel crystalline polymorph. This invention also relates to an amorphous form of (2S,3S,5S)-5-(N-(N-((N-methyl-N-((2-isopropyl-4-thiazolyl)methyl)amino)-carbonyl)-L-valinyl)amino)-2-(N-((5-thiazolyl)methoxycarbonyl)amino)-1,6-diphenyl-3-hydroxyhexane and methods for its preparation

BACKGROUND OF THE INVENTION

Inhibitors of human immunodeficiency virus (HIV) protease have been approved for use in the treatment of HIV infection for several years. A particularly effective HIV protease inhibitor is (2S,3S,5S)-5-(N-(N-((N-methyl-N-((2-isopropyl-4-thiazolyl)methyl)amino)carbonyl)-L-valinyl)amino)-2-(N-((5-thiazolyl)-methoxycarbonyl)amino)-1,6-diphenyl-3-hydroxyhexane (ritonavir), which is marketed as NORVIR®. Ritonavir is known to have utility for the inhibition of HIV protease, the inhibition of HIV infection, the inhibition of cytochrome P450 monooxygenase and the enhancement of the pharmacokinetics of compounds which are metabolized by cytochrome P450 monooxygenase. Ritonavir is particularly effective for the inhibition of HIV infection when used alone or in combination with one or more reverse transcriptase inhibitors and/or one or more other HIV protease inhibitors.

Ritonavir and processes for its preparation are disclosed in U.S. Pat. No. 5,541,206, issued Jul. 30, 1996. This patent discloses processes for preparing ritonavir which produce a crystalline polymorph of ritonavir which is termed crystalline Form I. Substantially pure Form I has the powder X-ray diffraction pattern, $^{13}C$ solid state nuclear magnetic resonance spectrum, the FT near infrared spectrum and the FT mid infrared spectrum which appear in FIGS. 1, 4, 6 and 8, respectively. The angular positions (two theta) of the characteristic peaks in the powder X-ray diffraction pattern of substantially pure Form I shown in FIG. 1 are 3.33°±0.1°, 6.76°±0.1°, 8.33°±0.1°, 14.61°±0.1°, 16.33°±0.1°, 16.76°±0.1°, 17.03°±0.1°, 18.02°±0.1°, 18.62°±0.1°, 19.47°±0.1°, 19.86°±0.1°, 20.25°±0.1°, 21.46°±0.1°, 23.46°±0.1° and 24.36°±0.1°.

Another process for the preparation of ritonavir is disclosed in U.S. Pat. No. 5,567,823, issued Oct. 22, 1996. The process disclosed in this patent also produces ritonavir as crystalline Form I.

Pharmaceutical compositions comprising ritonavir or a pharmaceutically acceptable salt thereof are disclosed in U.S. Pat. No. 5,541,206, issued Jul. 30, 1996; U.S. Pat. No. 5,484,801, issued Jan. 16, 1996; U.S. Pat. No. 5,725,878, issued Mar. 10, 1998; and U.S. Pat. No. 5,559,158, issued Sep. 24, 1996 and in International Application No. WO98/22106, published May 28, 1998 (corresponding to U.S. Ser. No. 08/966,495, filed Nov. 7, 1997).

The use of ritonavir to inhibit an HIV infection is disclosed in U.S. Pat. No. 5,541,206, issued Jul. 30, 1996. The use of ritonavir in combination with one or more reverse transcriptase inhibitors to inhibit an HIV infection is disclosed in U.S. Pat. No. 5,635,523, issued Jun. 3, 1997. The use of ritonavir in combination with one or more HIV protease inhibitors to inhibit an HIV infection is disclosed in U.S. Pat. No. 5,674,882, issued Oct. 7, 1997. The use of ritonavir to inhibit cytochrome P450 monooxygenase and to enhance the pharmacokinetics of compounds metabolized by cytochrome P450 monooxygenase is disclosed in WO97/01349, published Jan. 16, 1997 (corresponding to U.S. Ser. No. 08/687,774, filed Jun. 26, 1996).

It has now been unexpectedly discovered that ritonavir can be prepared as a new crystalline polymorph which is termed crystalline Form II.

All publications, issued patents and patent applications cited herein are hereby incorporated by reference.

BRIEF DESCRIPTION OF THE DRAWINGS

FIG. 8 is the FT mid infrared spectrum of the substantially pure Form I crystalline polymorph of ritonavir.

FIG. 9 is the FT mid infrared spectrum of the substantially pure Form II crystalline polymorph of ritonavir.

FIG. 10 is the differential scanning calorimetric thermogram for substantially pure amorphous ritonavir.

DISCLOSURE OF THE INVENTION

In accordance with the present invention, there is a novel substantially pure crystalline polymorph of (2S,3S,5S)-5-(N-(N-((N-methyl-N-((2-isopropyl-4-thiazolyl)methyl)amino)carbonyl)-L-valinyl)amino)-2-(N-((5-thiazolyl)-methoxycarbonyl)amino)-1,6-diphenyl-3-hydroxyhexane (ritonavir). For the sake of identification, this crystalline polymorph is designated as the Form II crystalline polymorph of ritonavir.

Substantially pure Form II has the powder X-ray diffraction pattern, $^{13}C$ solid state nuclear magnetic resonance spectrum, the FT near infrared spectrum and the FT mid infrared spectrum which appear in FIGS. 2, 5, 7 and 9, respectively.

Figure 1:
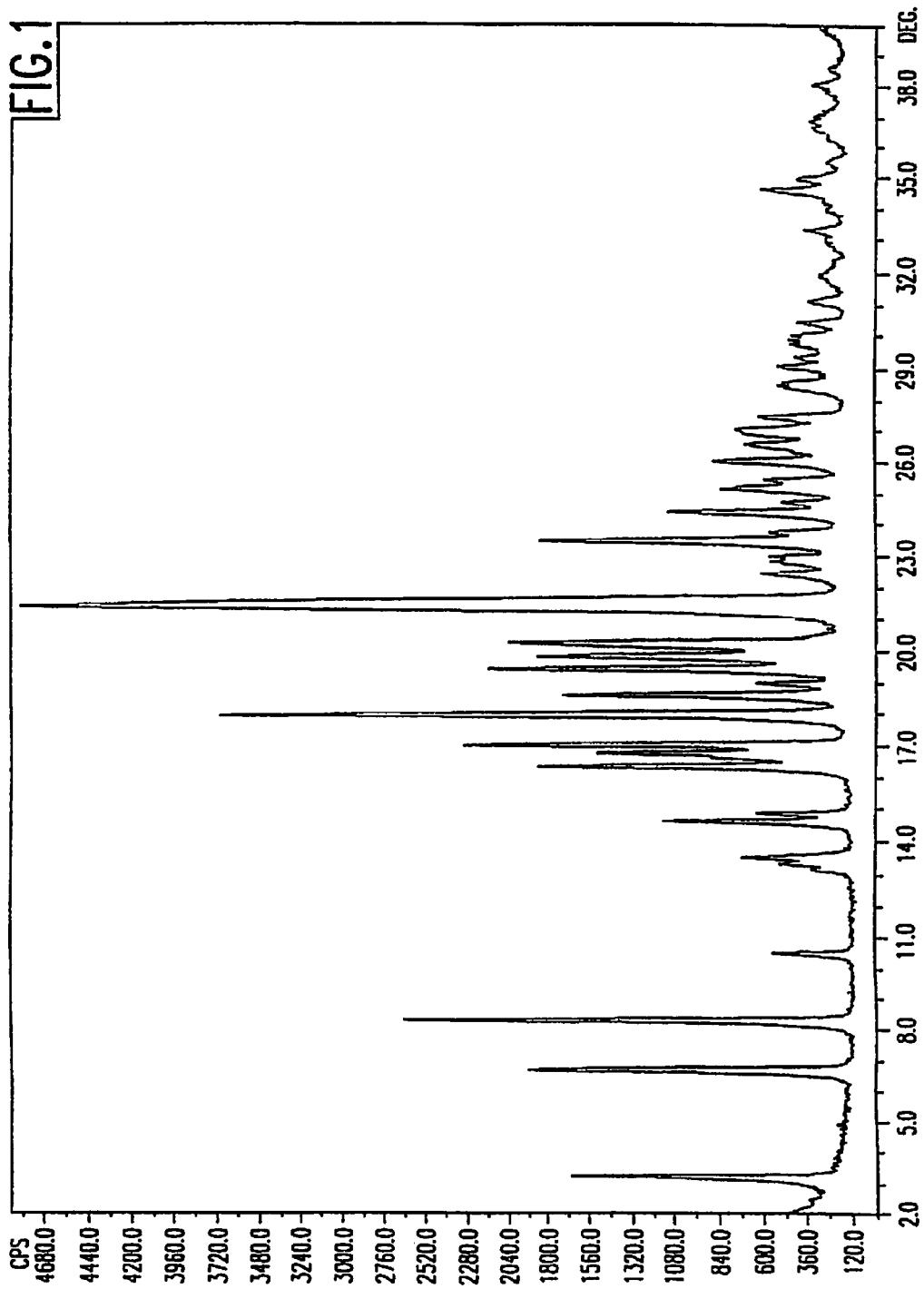
FIG. 1 is the powder X-ray diffraction pattern of the substantially pure Form I crystalline polymorph of ritonavir.
Figure 2:
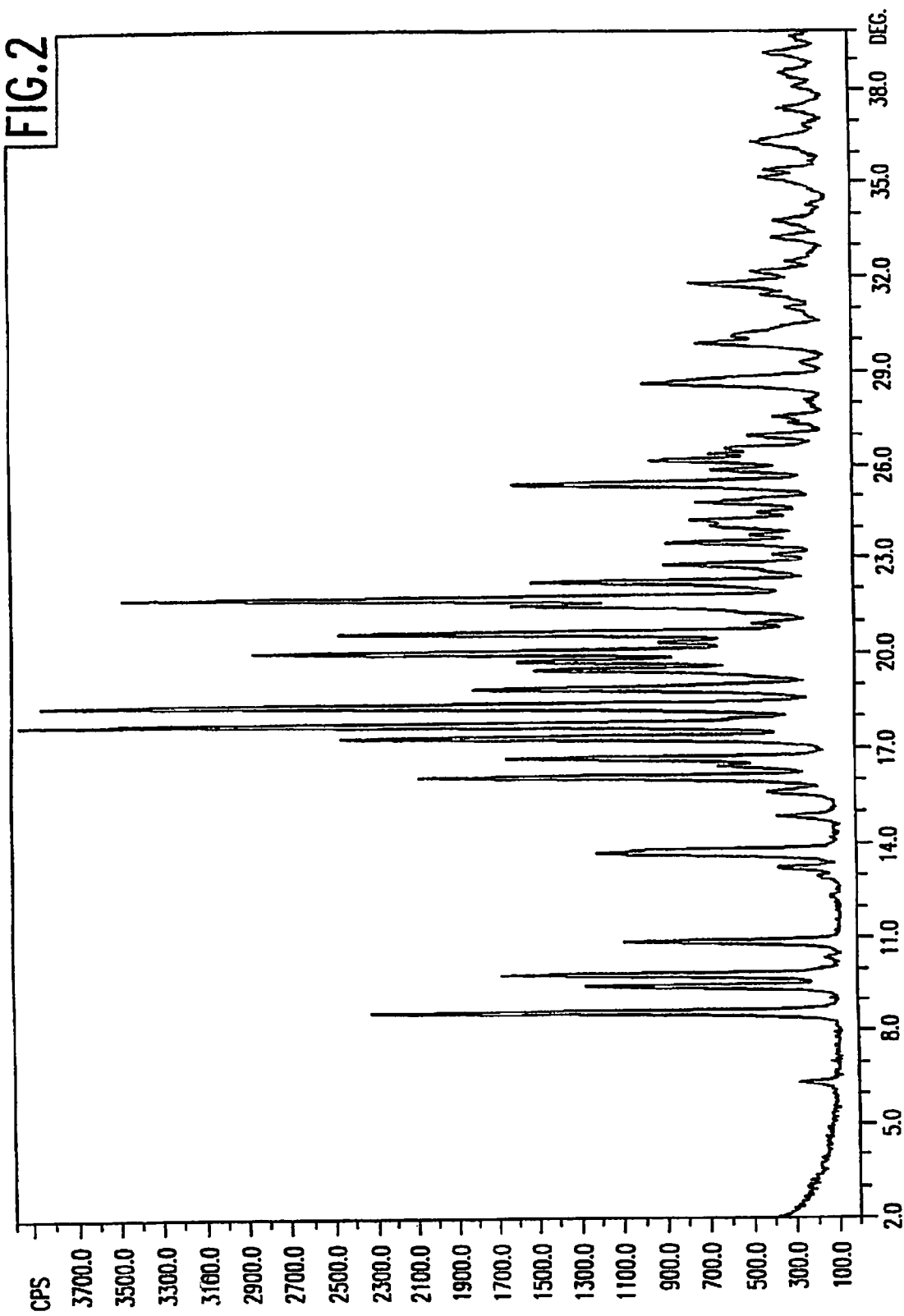
FIG. 2 is the powder X-ray diffraction pattern of the substantially pure Form II crystalline polymorph of ritonavir.
Figure 3:
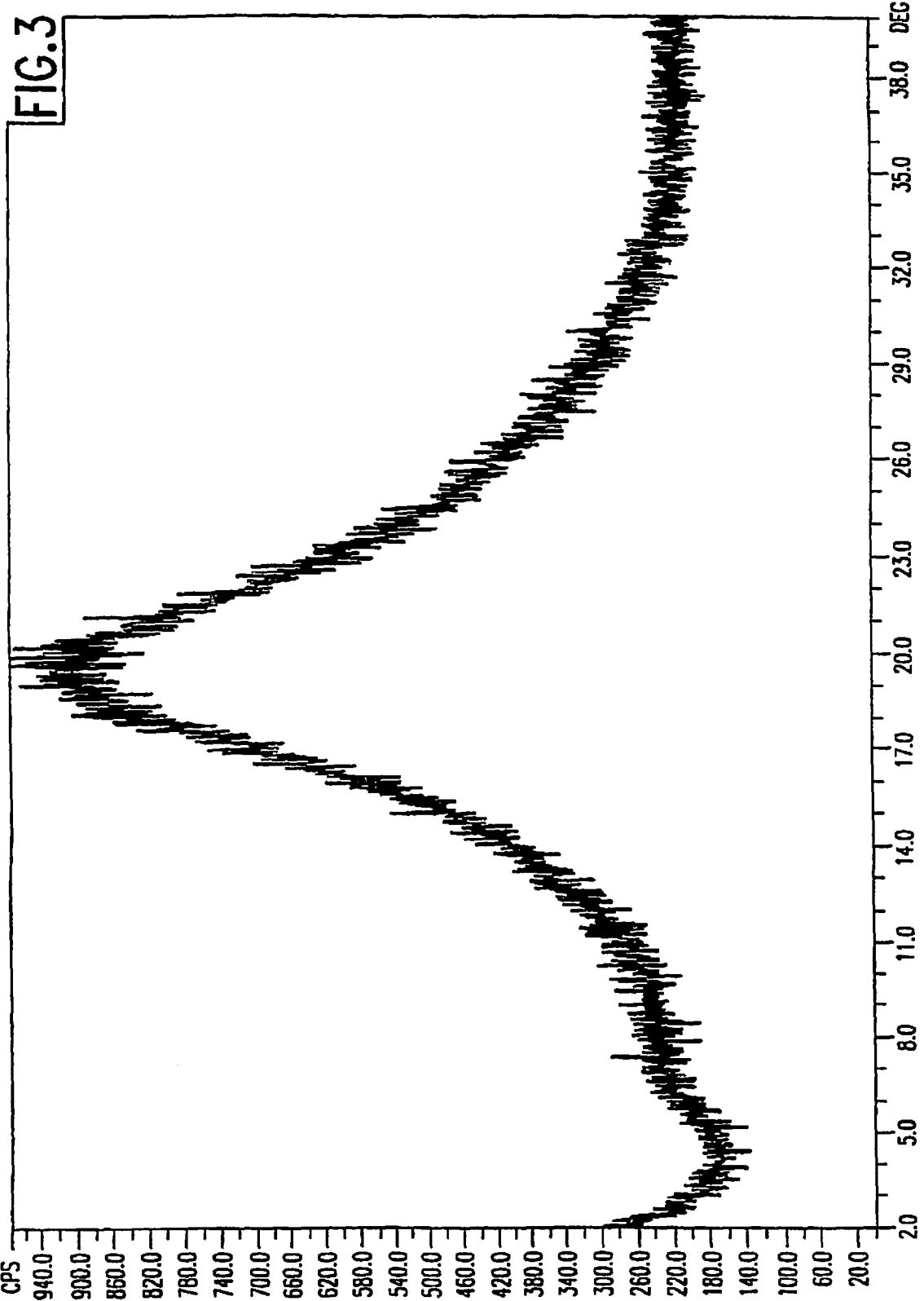
FIG. 3 is the powder X-ray diffraction pattern of substantially pure amorphous ritonavir.
Figure 4:
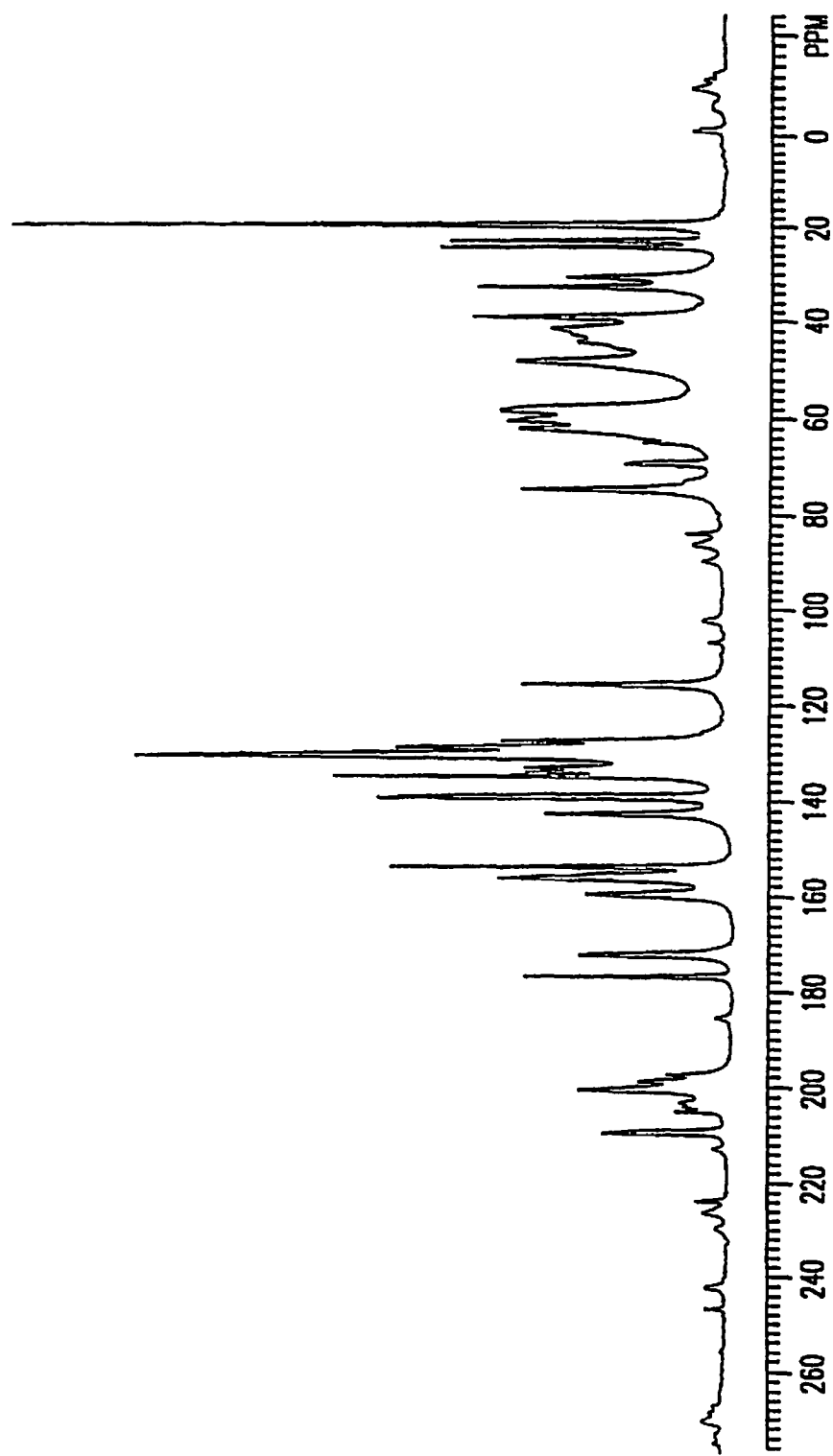
FIG. 4 is the 400 MHz solid state $^{13}C$ nuclear magnetic resonance spectrum of the substantially pure Form I crystalline polymorph of ritonavir.
Figure 5:
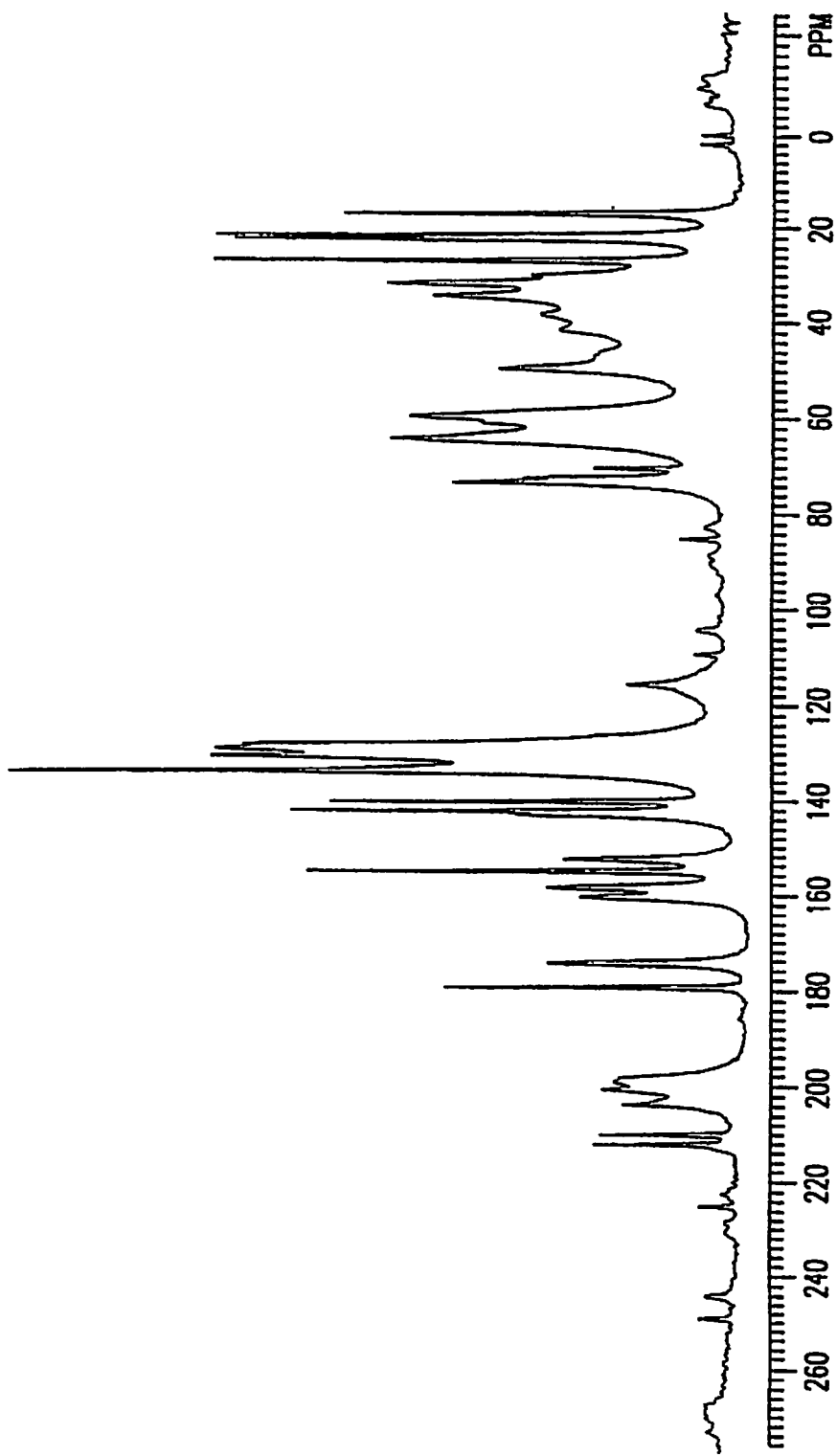
FIG. 5 is the 400 MHz solid state $^{13}C$ nuclear magnetic resonance spectrum of the substantially pure Form II crystalline polymorph of ritonavir.
Figure 6:
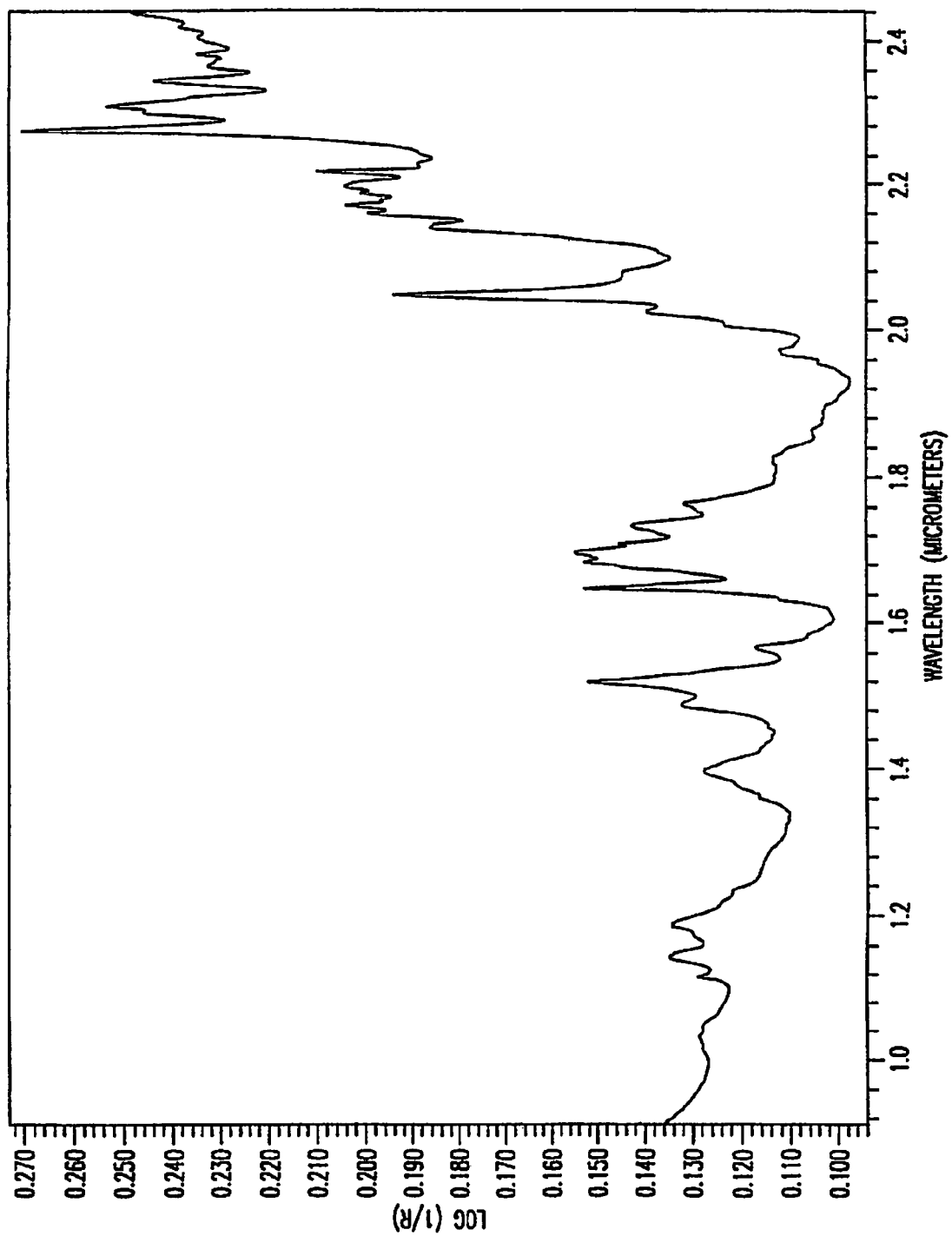
FIG. 6 is the FT near infrared spectrum of the substantially pure Form I crystalline polymorph of ritonavir.
Figure 7:
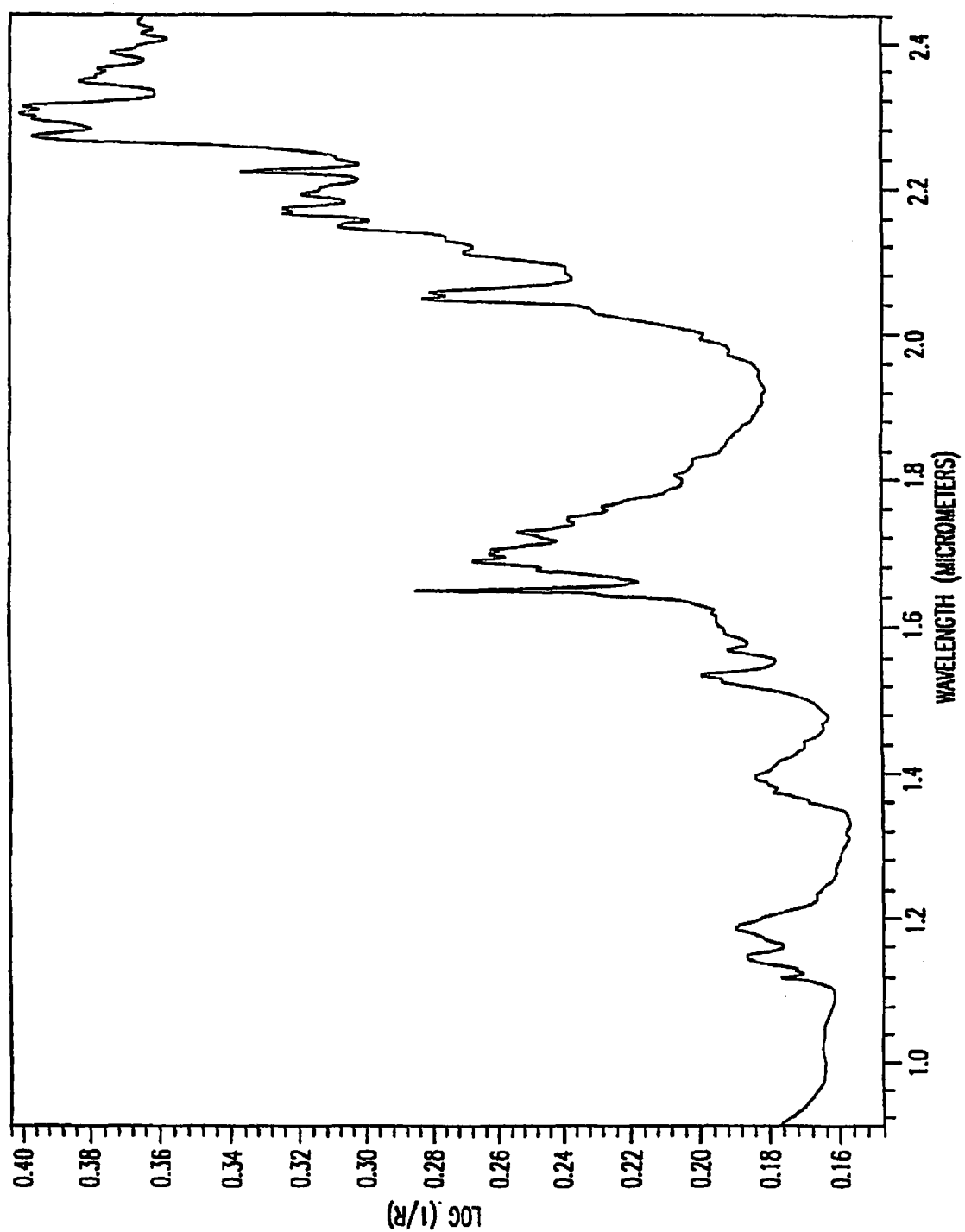
FIG. 7 is the FT near infrared spectrum of the substantially pure Form II crystalline polymorph of ritonavir.

The two-theta angle positions of characteristic peaks in the powder X-ray diffraction pattern of substantially pure Form II as shown in FIG. 2 are:
8.67°±0.1°, 9.88°±0.1°, 16.11°±0.1°, 16.70°±0.1°, 17.36°±0.1°, 17.78°±0.1°, 18.40°±0.1°, 18.93°±0.1°, 20.07°±0.1°, 20.65°±0.1°, 21.71°±0.1° and 25.38°±0.1°.

More preferably, substantially pure Form II is characterized by peaks in the powder X-ray diffraction pattern having two-theta angle positions as shown in FIG. 2 of:
8.67°±0.1°, 9.51°±0.1°, 9.88°±0.1°, 10.97°±0.1°, 13.74°±0.1°, 16.11°±01°, 16.70°±0.1°, 17.36°±0.1°, 17.78°±0.1°, 18.40°±0.1°, 18.93°±0.1°, 19.52°±0.1°, 19.80°±0.1°, 20.07°±0.1°, 20.65°±0.1°, 21.49°±0.1°, 21.71°±0.1°, 22.23°±0.1°, 25.38°±0.1°, 26.15°±0.1° and 28.62°±0.1°.

The substantially pure Form II crystalline polymorph of ritonavir can be prepared from amorphous ritonavir by contacting amorphous ritonavir with a C1-C3 alcohol. The method of contacting may be either by saturating the amorphous compound in the solvent at ambient temperature and then allowing the mixture to stand for an extended period of time (for example, overnight) or by dissolving the amorphous compound in the solvent at elevated temperature, preferably, at reflux, followed by cooling the solution to room temperature and isolating Form II.

In one embodiment of the process, the substantially pure Form II crystalline polymorph of ritonavir can be prepared from amorphous ritonavir by preparing a saturated solution of amorphous ritonavir in a C1-C3 alcohol at room temperature and isolating Form II which results. In practice this can be accomplished by dissolving a sufficient amount of amorphous ritonavir in the C1-C3 alcohol at elevated temperature (up to reflux) such that when the solution is allowed to cool to room temperature a saturated solution is obtained, from which Form II precipitates and can be isolated. A preferred solvent for the preparation of Form II is anhydrous ethanol. Isolation of the resulting solid provides Form II.

Substantially pure amorphous ritonavir is prepared from the Form I crystalline polymorph of ritonavir by melting Form I ritonavir and rapidly cooling the melt. Isolation of the resulting solid provides amorphous ritonavir.

Substantially pure amorphous ritonavir can also be prepared by slowly adding a solution of ritonavir Form I in a suitable solvent (methylene chloride and the like; preferably, methylene chloride) at a concentration of, preferably, about 1 g of ritonavir per about 1.5-2.0 mL of solvent (preferably, about 1 g of ritonavir/ about 1.5 mL of methylene chloride) to an anti-solvent (for example, hexane or heptane and the like; preferably, hexane) at a concentration of about 60-110 mL of antisolvent/g of ritonavir; preferably, about 85-90 mL of hexane/g of ritonavir, followed by isolation (for example, by filtration) of the resulting solid.

Similarly, substantially pure amorphous ritonavir can also be prepared by slowly adding a solution of ritonavir Form I in a suitable solvent such as methanol or the like at a concentration of, preferably, about 1 g of ritonavir per about 1.5-2.0 mL of solvent (preferably, about 1 g of ritonavir/ about 1.5 mL of methanol) to an anti-solvent such as methyl t-butyl ether (MTBE) or the like at a concentration of about 60-150 mL of antisolvent/g of ritonavir, preferably, about 90-110 mL of MTBE/g of ritonavir and, most preferably, about 100 mL of MTBE/g of ritonavir, followed by isolation (for example, by filtration) of the resulting solid.

Substantially pure amorphous ritonavir can also be prepared by slowly adding a solution of ritonavir Form I in a suitable solvent (for example, methanol and the like; preferably, methanol) at a concentration of about 1 g of ritonavir per about 1.5-2.0 mL of solvent (preferably, about 1 g of ritonavir/about 1.6 mL of methanol) to water at about 0° C. at a concentration of about 400-500 mL of water/g of ritonavir (preferably, about 400 mL of water/g of ritonavir), followed by isolation (for example, by filtration) and drying of the resulting solid.

Substantially pure amorphous ritonavir can also be prepared by lyophilization of a solution of ritonavir Form I. Preferred solvents are C1-C6 alcohols. A more preferred solvent is isobutanol.

Alternatively, in a preferred process, substantially pure Form II can be prepared by seeding a solution of ritonavir Form I in a suitable solvent (preferably, a C1-C3 alcohol; most preferably, ethanol) with undissolved (2S)-N-((1S)-1-Benzyl-2-((4S,5S)-4-benzyl-2-oxo-1,3-oxazolidin-5-yl)ethyl)-2-((((2-isopropyl-1,3-thiazol-4-yl)methyl)amino)-carbonyl)amino)-3-methylbutanamide. In a preferred method, ritonavir Form I is dissolved in ethanol (preferably, 200 proof ethanol) at a concentration of from about 150 g/L to about 200 g/L, preferably, about 160 g/L. To the solution is added seed crystals of (2S)-N-((1S)-1-Benzyl-2-((4S,5S)-4-benzyl-2-oxo-1,3-oxazolidin-5-yl)ethyl)-2-((((2-isopropyl-1,3-thiazol-4-yl)methyl)amino)carbonylyamino)-3-methylbutanamide in the amount of from about 0.02 g to about 0.10 g of seed crystals/g of ritonavir. The amount of seed crystals added is such that it exceeds the saturation amount in the solvent being used so that there are undissolved seed crystals present in the ritonavir solution. The mixture is allowed to stand at a temperature of from about 0° C. to about 15° C. (preferably, about 5° C.) for from about 12 hours to about 48 hours (preferably, about 24 hours). The resulting crystalline ritonavir Form II is isolated by filtration.

In yet another preferred alternative method, substantially pure Form II can be prepared by recrystallization of Form I or mixtures of Form I and Form II from a solution in a suitable solvent (for example, ethyl acetate or isopropyl acetate or chloroform and the like other solvents with like dielectric constant; preferably, ethyl acetate), with seeding with Form II crystals, followed by addition of an anti-solvent (for example, heptane, hexane, toluene, petroleum ether and the like other anti-solvents with like dielectric constant; preferably, heptane). The amount of seed crystals added is such that it exceeds the saturation amount in the solvent being used so that there are undissolved seed crystals present in the ritonavir solution. In a preferred method, ritonavir (Form I or a mixture of Form I and Form II) is dissolved in ethyl acetate (from about 4.0 L to about 6.0 L/kg of ritonavir) with heating (at from about 65° C. to about 70° C.). The solution is slowly cooled to from about 55° C. to about 50° C., preferably about 52° C. Seed crystals of ritonavir Form II (from about 0.5 g of Form II seed crystals/kg of ritonavir to about 10.0 g of Form II seed crystals/kg of ritonavir, preferably about 1.25 g of Form II seed crystals/kg of ritonavir) are added and the mixture is stirred for about 1 hour at a temperature of from about 55° C. to about 50° C., preferably about 52° C. The amount of seed crystals added is such that it exceeds the saturation amount in the solvent being used so that there are undissolved seed crystals present in the ritonavir solution. Heptane (from about 1.0 L/kg of ritonavir to about 4.0 L/kg of ritonavir; preferably, about 2.8 L/kg of ritonavir) is added with mixing and the mixture is allowed to slowly cool to about 25° C. and is then stirred for at least 12 hours at about 25° C. The product is isolated by filtration/centrifugation and is dried under vacuum with heating. On a manufacturing scale (300-400 kg batches), it has been observed that isolation by filtration/ centrifugation is considerably faster for Form II than for the corresponding amount of Form I (16 hours versus 24-30 hours).

It has also been found that Form II or mixtures of Form II and Form I can be converted to substantially pure Form I by dissolving the Form II or mixture of Form II and Form I in a suitable solvent (for example, ethyl acetate or isopropyl acetate and the like; preferably, ethyl acetate) at a concentration of about 1 kg of ritonavir/4 L of solvent (preferably, ethyl acetate) with heating. The hot solution of ritonavir is slowly added (preferably, through a filter) to a slurry of seed crystals of ritonavir Form I (from about 0.5% to about 10% by weight relative to amount of ritonavir Form II or mixture of Form II and Form I; preferably, from about 0.5% to about 5% by weight and, most preferably, from about 0.5% to about 1% by weight) in an anti-solvent (for example, heptane or hexane and the like; preferably, heptane) at a concentration of about 1 kg of ritonavir (Form II or mixture of Form II and Form I) per about 4-8 L of antisolvent (preferably, about 1 kg of ritonavir (Form II or mixture of Form II and Form I)/about 4 L of heptane). The mixture is cooled to about 20° C. and stirred for at least 3 hours. Isolation (for example, by filtration) and drying of the resulting solid provides ritonavir Form I.

The following examples will serve to further illustrate the preparation of the novel forms of ritonavir of the invention and the conversion of Form II to Form I.

EXAMPLE 1

Preparation of Amorphous Ritonavir

Form I crystalline polymorph of ritonavir (100 g) was melted at 125° C. by heating Form I. The melt was maintained at a temperature of 125° C. for 3 hours. The melt was rapidly cooled by placing the container holding the melt into a Dewar flask containing liquid nitrogen. The resulting glass was ground with a mortar and pestle to provide amorphous ritonavir (100 g). Powder X-ray diffraction analysis confirmed that the product was amorphous. Differential scanning calorimetric analysis determined that the glass transition point was from about 45° C. to about 49° C. (Measured onset at 45.4° C. and which ends at 49.08° C., with a midpoint of 48.99° C.).

EXAMPLE 2

Preparation of Crystalline Ritonavir (Form II)

Amorphous ritonavir (40.0 g) was dissolved in boiling anhydrous ethanol (100 mL). Upon allowing this solution to cool to room temperature, a saturated solution was obtained. After standing overnight at room temperature, the resulting solid was isolated from the mixture by filtration and was air dried to provide Form II (approximately 24.0 g).

EXAMPLE 3

Preparation of (2S)-N-((1S)-1-Benzyl-2-((4S,5S)-4-benzyl-2-oxo-1,3-oxazolidin-5-yl)ethyl)-2-((((2-isopropyl-1,3-thiazol-4-yl)methyl)amino)carbonyl)amino)-3-methylbutanamide

EXAMPLE 3a

Preparation of (4S,5S)-5-((2S)-2-t-butyloxycarbonylamino-3-phenylpropyl)-4-benzyl-1,3-oxazolidin-2-one (2S,3S,5S)-2-Amino-3-hydroxy-5-t-butyloxycarbonylamino-1,6-diphenylhexane succinate salt (30 g, 63 mmol; U.S. Pat. No. 5,654,466), ((5-thiazolyl)methyl)-(4-nitrophenyl)carbonate hydrochloride (22.2 g; U.S. Pat. No. 5,597,926) and sodium bicarbonate (16.2 g) were mixed with 300 mL of water and 300 mL of ethyl acetate and the mixture was stirred at room temperature for about 30 minutes. The organic layer was then separated and heated at about 60° C. for 12 hours, and then stirred at 20-25° C. for 6 hours. 3 mL of ammonium hydroxide (29% ammonia in water) was added and the mixture stirred for 1.5 hours. The resulting mixture was washed with 4×200 mL of 10% aqueous potassium carbonate and the organic layer was separated and evaporated under vacuum to provide an oil. The oil was suspended in about 250 mL of heptane. The heptane was evaporated under vacuum to provide a yellow solid. The yellow solid was dissolved in 300 mL of THF and 25 mL of 10% aqueous sodium hydroxide was added. After stirring for about 3 hours, the mixture was adjusted to pH 7 by addition of 4N HCl (about 16 mL). The THF was evaporated under vacuum to leave an aqueous residue, to which was added 300 mL of distilled water. After stirring this mixture, a fine suspension of solids resulted. The solid was collected by filtration and the filtered solid was washed with water (1400 mL) in several portions, resulting in the desired product.

EXAMPLE 3b

Preparation of (4S,5S)-5-((2S)-2-amino-3-phenylpropyl)-4-benzyl-1,3-oxazolidin-2-one The crude, wet product of Example 3a was slurried in 1N HCl (192 mL) and the slurry was heated to 70° C. with stirring. After 1 hour, THF (100 mL) was added and stirring at 65° C. was continued for 4 hours. The mixture was then allowed to cool to 20-25° C. and was stirred overnight at 20-25° C. The THF was removed by evaporation under vacuum and the resulting aqueous solution was cooled to about 5° C., causing some precipitation to occur. The aqueous mixture was adjusted to pH 7 by addition of 50% aqueous sodium hydroxide (about 18.3 g). The resulting mixture was extracted with ethyl acetate (2×100 mL) at about 15° C. The combined organic extracts were washed with 100 mL of brine and the organic layer was separated and stirred with sodium sulfate (5 g) and Darco G-60 (3 g). This mixture was warmed on a hot plate for 1 hour at 45° C. The hot mixture was then filtered through a bed of diatomaceous earth and the filter pad was washed with ethyl acetate (100 mL). The filtrate was evaporated under vacuum to provide an oil. The oil was redissolved in methylene chloride (300 mL) and the solvent was evaporated under vacuum. The resulting oil was dried at room temperature under vacuum to provide the desired product (18.4 g) as a glassy syrup.

EXAMPLE 3c

Preparation of (2S)-N-((1S)-1-Benzyl-2-((4S,5S)-4-benzyl-2-oxo-1,3-oxazolidin-5-yl)ethyl)-2-((((2-isopropyl-1,3-thiazol-4-yl)methyl)amino)carbonyl)amino)-3-methylbutanamide N-((N-Methyl-N((2-isopropyl-4-thiazolyl)methyl)amino)carbonyl)-L-valine (10.6 g, 33.9 mmol; U.S. Pat. No. 5,539,122 and International Patent Application No. WO98/00410), the product of Example 3b (10.0 g, 32.2 mmol) and 1-hydroxybenzotriazole (5.2 g, 34 mmol) were dissolved in THF (200 mL). 1,3-dicyclohexylcarbodiimide (DCC, 7.0 g, 34 mmol) was then added to the THF mixture and the mixture was stirred at 22° C. for 4 hours. Citric acid (25 mL of 10% aqueous solution) was added and stirring continued for 30 minutes. The THF was then evaporated under vacuum. The residue was dissolved in ethyl acetate (250 mL) and washed with 10% citric acid solution (175 mL). NaCl (5 g) was added to accelerate the separation of the layers. The organic layer was sequentially washed with 10% aq. sodium carbonate (2×200 mL) and water (200 mL). The organic layer was then dried over sodium sulfate (20 g), filtered and evaporated under vacuum. The resulting product (20.7 g of a foam) was dissolved in hot ethyl acetate (150 mL) and then heptane (75 mL) was added. Upon cooling, another 75 mL of heptane was added and the mixture was heated to reflux. Upon cooling to room temperature, no precipitate formed. The solvents were evaporated under vacuum and the residue was redissolved in a mixture of 200 mL ethyl acetate/100 mL heptane. The small amount of undissolved solid was removed by filtration. The filtrate was evaporated under vacuum and the residue was dissolved in a mixture of 100 mL ethyl acetate/50 mL heptane, giving a clear solution. The solution was cooled to −10° C. and a white precipitate formed. The mixture was allowed to sit at −15° C. for 24 hours. The resulting solid was collected by filtration, washed with 1:1 ethyl acetate/heptane (2×24 mL) and dried in a vacuum oven at 55° C. to provide the desired product as a beige solid (16.4 g).

$^1$H NMR (DMSO-$d_6$) δ 7.84 (1H, doublet J=8.6), 7.71 (1H, singlet), 7.32-7.11 (11H, multiplet), 6.09 (1H, doublet J=8.5), 4.51 (1H AB J=16.2), 4.43 (1H AB J=16.2), 4.22 (1H, multiplet), 4.07 (1H, multiplet), 3.96 (1H, doublet of doublet J=7.3,7.4), 3.65 (1H, multiplet), 3.23 (1H, septuplet J=6.9), 2.89 (3H, singlet), 2.84-2.60 (4H, multiplet), 1.94 (1H, multiplet), 1.76-1.49 (2H, multiplet), 1.30 (6H, doublet J=6.9), 0.80 (3H, doublet J=5.8), 0.77 (3H, doublet J=5.8)

$^{13}$C NMR (DMSO-$d_6$) δ 177.2, 171.5, 157.6, 157.5, 152.8, 138.3, 136.5, 129.5, 129.2, 128.2, 128.0, 126.4, 126.0, 114.0, 77.2, 59.9, 57.6, 48.2, 46.2, 40.4, 40.1, 39.1, 34.5, 32.4, 30.3, 22.8, 22.8, 19.4, 18.3.

EXAMPLE 4

Preparation of Crystalline Ritonavir (Form II)

To a solution of 1.595 g of ritonavir Form I in 10 mL of 200 proof ethanol was added an amount of the product of Example 3c (approximately 50 micrograms) such that all of the added amount of the product of Example 3c did not dissolve. This mixture was allowed to stand at about 5° C. for 24 hours. The resulting crystals were isolated by filtration through 0.45 micron nylon filter and air dried to provide ritonavir Form II.

EXAMPLE 5

Alternative Preparation of Crystalline Ritonavir (Form II)

Ethyl acetate (6.0 L/kg of ritonavir) was added to ritonavir (Form I or a mixture of Form I and Form II) in a reaction vessel. The mixture was stirred and heated to 70° C. until all solids were dissolved. The solution was filtered (utilizing a centrifuge pump and 5×20 inch cartridge filters having a porosity of 1.2 microns) and the filtrate was allowed to cool to 52° C. at a rate of 2-10° C./hour. To this solution was added an amount of ritonavir Form II seed crystals (about 1.25 g of Form II seed crystals/kg of ritonavir) such that all of the seed crystals did not dissolve and the mixture was stirred at 52° C. for not less than 1 hour at an agitation rate of 15 RPM. The mixture was then allowed to cool to 40° C. at a rate of 10° C./hour. Heptane (2.8 L/kg of ritonavir) was added at a rate of 7 L/minute with mixing. The mixture was allowed to cool to 25° C. at a rate of 10° C./hour with mixing. Then the mixture was stirred for not less than 12 hours at 25° C. The product was isolated by filtration using a Heinkel type centrifuge (run time approximately 16 hours). The product was dried at 55° C. under vacuum (50 mm Hg) for 16-25 hours to provide ritonavir crystal Form II.

EXAMPLE 6

Preparation of Amorphous Ritonavir

Ritonavir Form I (40 g) was dissolved in methylene chloride (60 mL). This solution was slowly added over 15 minutes to a round bottom flask equipped with an overhead stirrer and containing hexanes (3.5 L). The resulting slurry was allowed to stir for 10 minutes. The precipitate was filtered and dried at room temperature in a vacuum oven to provide amorphous ritonavir (40 g).

EXAMPLE 7

Preparation of Amorphous Ritonavir

Ritonavir Form I (5 g) was dissolved in methanol (8 mL). This solution was slowly added to a round bottom flask equipped with an overhead stirrer and containing distilled water (2 L), while maintaining the internal temperature near 0° C. The resulting solid was filtered to give a sticky solid which was dried in a vacuum oven at 20-25° C. for 12-18 hours to give amorphous ritonavir (2.5 g).

EXAMPLE 8

Preparation of Ritonavir Form I

Ritonavir Form II (1 kg) was added to a reactor (A), followed by the addition of ethyl acetate (4 L). This mixture was refluxed until all of the solids were dissolved.

To a separate reactor (B) was added an amount of seed crystals of ritonavir Form I (5 g), followed by the addition of heptane (4 L), such that all of the seed crystals did not dissolve. This mixture (a slurry) was stirred at 23° C.±5° C.

The hot solution from reactor A was slowly filtered, using a 0.2 micron filter cartridge, into the mixture in reactor B over not less than 2 hours. The resulting slurry in reactor B was cooled to 20° C. and stirred for not less than 3 hours. The resulting slurry was filtered, the filtered solid washed with heptane and then dried in a vacuum oven at 65° C. to provide ritonavir Form I.

A preferred pharmaceutical composition comprising ritonavir, especially, ritonavir Form II, has the following composition, encapsulated in a soft elastic gelatin capsule.

| | |
|---|---|
| Ritonavir Form II | 100.0 mg |
| Ethanol, dehydrated | 120.0 mg |
| Oleic acid | 709.75 mg |
| Butylated hydroxytoluene | 0.25 mg |
| Polyoxyl 35 castor oil (Cremophor EL ®) | 60.0 mg |
| Water | 10.0 mg |

The preferred composition can be prepared according to the following method.

The following protocol is employed in the preparation of 1000 soft gelatin capsules:

| Scale (mg/capsule) | Name | Amount (g) |
|---|---|---|
| Q.S. | Nitrogen, N.F. | Q.S. |
| 118.0 | Ethanol, dehydrated, USP, 200 Proof | 118.0 |
| 2.0 | Ethanol, dehydrated, USP, 200 Proof | 2.0 |
| 0.25 | Butylated Hydroxytoluene, NF | 0.25 |
| 704.75 | Oleic Acid, NF | 704.75 |
| 100.0 | Ritonavir Form II | 100.0 |
| 10.0 | Water, purified, USP (distilled) | 10.0 |
| 60.0 | Polyoxyl 35 Castor Oil, NF | 60.0 |
| 5.000 | Oleic Acid, NF | 5.000 |

A mixing tank and suitable container are purged with nitrogen. 118.0 g of ethanol is weighed, blanketed with nitrogen, and held for later use. The second aliquot of ethanol (2 g) is then weighed, and mixed with 0.25 g of butylated hydroxytoluene until clear. The mixture is blanketed with nitrogen and held. The main mixing tank is heated to 28° C. (not to exceed 30° C.). 704.75 g of oleic acid is then charged into the mixing tank. 100.0 g of ritonavir Form II is then added to the oleic acid with mixing. The ethanol/butylated hydroxytoluene is then added to the mixing tank, followed by the 118.0 g of ethanol measured previously, and mixed for at least 10 minutes. 10 g of water is then charged into the tank and mixed until the solution is clear (for not less than 30 minutes). 60.0 g of Polyoxyl 35 castor oil is charged into the tank and mixed until uniform. The solution is stored at 2-8° C. until encapsulation. According to the procedures described in International Patent Application WO98/22106, 1.0 g of the solution is filled into each soft gelatin capsule and the soft gelatin capsules are then dried, and stored at 2-8° C.

As used herein, the term "substantially pure", when used in reference to a polymorph of ritonavir, refers to a polymorph of ritonavir, Form I or Form II, which is greater than about 90% pure. This means that the polymorph of ritonavir does not contain more than about 10% of any other compound and, in particular, does not contain more than about 10% of any other form of ritonavir. More preferably, the term "substantially pure" refers to a polymorph of ritonavir, Form I or Form II, which is greater than about 95% pure. This means that the polymorph of ritonavir does not contain more than about 5% of any other compound and, in particular, does not contain more than about 5% of any other form of ritonavir. Even more preferably, the term "substantially pure" refers to a polymorph of ritonavir, Form I or Form II, which is greater than about 97% pure. This means that the polymorph of ritonavir does not contain more than about 3% of any other compound and, in particular, does not contain more than about 3% of any other form of ritonavir.

As used herein, the term "substantially pure", when used in reference to amorphous ritonavir, refers to amorphous ritonavir which is greater than about 90% pure. This means that the amorphous ritonavir does not contain more than about 10% of any other compound and, in particular, does not contain more than about 10% of any other form of ritonavir. More preferably, the term "substantially pure", when used in reference to amorphous ritonavir, refers to amorphous ritonavir which is greater than about 95% pure. This means that the amorphous ritonavir does not contain more than about 5% of any other compound and, in particular, does not contain more than about 5% of any other form of ritonavir. Even more preferably, the term "substantially pure", when used in reference to amorphous ritonavir, refers to amorphous ritonavir which is greater than about 97% pure. This means that the amorphous ritonavir does not contain more than about 3% of any other compound and, in particular, does not contain more than about 3% of any other form of ritonavir.

Powder X-ray diffraction analysis of samples was conducted in the following manner. Samples for X-ray diffraction analysis were prepared by spreading the sample powder (with no prior grinding required) in a thin layer on the sample holder and gently flattening the sample with a microscope slide. A Nicolet 12/V X-ray Diffraction System was used with the following parameters: X-ray source: Cu-K$\alpha$1; Range: 2.00-40.00° Two Theta; Scan Rate: 1.00 degree/minute; Step Size: 0.02 degrees; Wavelength: 1.540562 angstroms.

Characteristic powder X-ray diffraction pattern peak positions are reported for polymorphs in terms of the angular positions (two theta) with an allowable variability of ±0.1°. This allowable variability is specified by the U.S. Pharmacopeia, pages 1843-1844 (1995). The variability of ±0.1° is intended to be used when comparing two powder X-ray diffraction patterns. In practice, if a diffraction pattern peak from one pattern is assigned a range of angular positions (two theta) which is the measured peak position ±0.1° and a diffraction pattern peak from the other pattern is assigned a range of angular positions (two theta) which is the measured peak position ±0.1° and if those ranges of peak positions overlap, then the two peaks are considered to have the same angular position (two theta). For example, if a diffraction pattern peak from one pattern is determined to have a peak position of 5.20°, for comparison purposes the allowable variability allows the peak to be assigned a position in the range of 5.10°-5.30°. If a comparison peak from the other diffraction pattern is determined to have a peak position of 5.35°, for comparison purposes the allowable variability allows the peak to be assigned a position in the range of 5.25°-5.45°. Because there is overlap between the two ranges of peak positions (i.e., 5.10°-5.30° and 5.25°-5.45°) the two peaks being compared are considered to have the same angular position (two theta).

Solid state nuclear magnetic resonance analysis of samples was conducted in the following manner. A Bruker AMX-400 MHz instrument was used with the following parameters: CP-MAS (cross-polarized magic angle spinning); spectrometer frequency for $^{13}C$ was 100.627952576 MHz; pulse sequence was cp2lev; contact time was 2.5 milliseconds; temperature was 27.0° C.; spin rate was 7000 Hz; relaxation delay was 6.000 sec; $1^{st}$ pulse width was 3.8 microseconds; $2^{nd}$ pulse width was 8.6 microseconds; acquisition time was 0.034 seconds; sweep width was 30303.0 Hz; 2000 scans.

FT near infrared analysis of samples was conducted in the following manner. Samples were analyzed as neat, undiluted powders contained in a clear glass 1 dram vial. A Nicolet Magna System 750 FT-IR spectrometer with a Nicolet SabIR near infrared fiber optic probe accessory was used with the following parameters: the source was white light; the detector was PbS; the beamsplitter was CaF2; sample spacing was 1.0000; digitizer bits was 20; mirror velocity was 0.3165; the aperture was 50.00; sample gain was 1.0; the high pass filter was 200.0000; the low pass filter was 11000.0000; the number of sample scans was 64; the collection length was 75.9 seconds; the resolution was 8.000; the number of scan points was 8480; the number of FFT points was 8192; the laser frequency was 15798.0 cm −1; the interferogram peak position was 4096; the apodization was Happ-Genzel; the number of background scans was 64 and the background gain was 1.0.

FT mid infrared analysis of samples was conducted in the following manner. Samples were analyzed as neat, undiluted powders. A Nicolet Magna System 750 FT-IR spectrometer with a Spectra-Tech InspectIR video microanalysis accessory and a Germanium attenuated total reflectance (Ge ATR) crystal was used with the following parameters: the source was infrared; the detector was MCT/A; the beamsplitter was KBr; sample spacing was 2.0000; digitizer bits was 20; mirror velocity was 1.8988; the aperture was 100.00; sample gain was 1.0; the high pass filter was 200.0000; the low pass filter was 20000.0000; the number of sample scans was 128; the collection length was 79.9 seconds; the resolution was 4.000; the number of scan points was 8480; the number of FFT points was 8192; the laser frequency was 15798.0 cm −1; the interferogram peak position was 4096; the apodization was triangular; the number of background scans was 128 and the background gain was 1.0.

Differential scanning calorimetric analysis of samples was conducted in the following manner. A T.A. Instruments Thermal Analyzer 3100 with Differential Scanning calorimetry module 2910 was used, along with Modulated DSC software version 1.1A. The analysis parameters were: Sample weight: 2.28 mg, placed in a covered, uncrimped aluminum pan; Heating rate: room temperature to 150° C. at 5° C./minute under a nitrogen purge.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for preparing a composition comprising ritonavir, said process comprising dissolving Form II and Form I crystalline ritonavir in a solvent, wherein said Form II crystalline ritonavir has characteristic peaks in a powder X-ray diffraction pattern at values of two theta of 8.67°±0.1°, 9.88°±0.1°, 16.11°±0.1°, 16.70°±0.1°, 17.36°±0.1°, 17.78°±0.1°, 18.40°±0.1°, 18.93°±0.1°, 20.07°±0.1°, 20.65°±0.1°, 21.71°±0.1° and 25.38°±0.1°, and said Form I crystalline ritonavir has characteristic peaks in a powder X-ray diffraction pattern at values of two theta of 3.33°±0.1°, 6.76°±0.1°, 8.33°±0.1°, 14.61°±0.1°, 16.33°±0.1°, 16.76°±0.1°, 17.03°±0.1°, 18.02°±0.1°, 18.62°±0.1°, 19.47°±0.1°, 19.86°±0.1°, 20.25°±0.1°, 21.46°±0.1°, 23.46°±0.1° and 24.36°±0.1°.

2. The process of claim 1, wherein said Form II crystalline ritonavir has characteristic peaks in a powder X-ray diffraction pattern at values of two theta of 8.67°±0.1°, 9.51°±0.1°, 9.88°±0.1°, 10.97°±0.1°, 13.74°±0.1°, 16.11°±0.1°, 16.70°±0.1°, 17.36°±0.1°, 17.78°±0.1°, 18.40°±0.1°, 18.93°±0.1°, 19.52°±0.1°, 19.80°±0.1°, 20.07°±0.1°, 20.65°±0.1°, 21.49°±0.1°, 21.71°±0.1°, 22.23°±0.1°, 25.38°±0.1°, 26.15°±0.1° and 28.62°±0.1°.

3. The process of claim 1, wherein said solvent is ethyl acetate.

4. The process of claim 1, wherein said solvent is isopropyl acetate.

5. The process of claim 1, wherein said solvent comprises ethanol and oleic acid.

6. A process of making ritonavir Form I, comprising mixing ritonavir dissolved in ethyl acetate with seed crystals of ritonavir Form I in heptane.

* * * * *

(12) EX PARTE REEXAMINATION CERTIFICATE (10495th)
United States Patent
Bauer et al.

(10) Number: US 8,674,112 C1
(45) Certificate Issued: *Feb. 3, 2015

(54) POLYMORPH OF A PHARMACEUTICAL

(75) Inventors: John F. Bauer, Lake Bluff, IL (US); Azita Saleki-Gerhardt, Libertyville, IL (US); Bikshandarkoil A. Narayanan, Newton, CT (US); Sanjay R. Chemburkar, Gurnee, IL (US); Ketan M. Patel, Wheeling, IL (US); Harry O. Spiwek, Kenosha, WI (US); Philip E. Bauer, Chester Springs, PA (US); Kimberly A. Allen, Trevor, WI (US)

(73) Assignee: AbbVie Inc., North Chicago, IL (US)

Reexamination Request:
No. 90/013,213, Apr. 11, 2014

Reexamination Certificate for:
Patent No.: 8,674,112
Issued: Mar. 18, 2014
Appl. No.: 13/480,882
Filed: May 25, 2012

( * ) Notice: This patent is subject to a terminal disclaimer.

Related U.S. Application Data

(60) Continuation of application No. 12/644,439, filed on Dec. 22, 2009, now Pat. No. 8,193,367, which is a continuation of application No. 11/524,972, filed on Sep. 21, 2006, now Pat. No. 7,659,405, which is a continuation of application No. 10/901,818, filed on Jul. 29, 2004, now Pat. No. 7,183,416, which is a division of application No. 09/356,736, filed on Jul. 19, 1999, now Pat. No. 6,894,171.

(60) Provisional application No. 60/093,432, filed on Jul. 20, 1998, provisional application No. 60/137,535, filed on Jun. 4, 1999.

(51) Int. Cl.
*C07D 417/12* (2006.01)
*C07D 277/28* (2006.01)

(52) U.S. Cl.
CPC ............ *C07D 277/28* (2013.01); *C07D 417/12* (2013.01)
USPC .......................................................... 548/204

(58) Field of Classification Search
None
See application file for complete search history.

(56) References Cited

To view the complete listing of prior art documents cited during the proceeding for Reexamination Control Number 90/013,213, please refer to the USPTO's public Patent Application Information Retrieval (PAIR) system under the Display References tab.

*Primary Examiner* — Dwayne Jones

(57) ABSTRACT

A new crystalline polymorph of ritonavir and methods for its use and preparation are disclosed.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 6 is determined to be patentable as amended.

Claims 1-5 were not reexamined.

6. A process of making ritonavir Form I, comprising mixing ritonavir *comprising ritonavir Form II* dissolved in ethyl acetate with seed crystals of ritonavir Form I in heptane *to provide ritonavir Form I*.

\* \* \* \* \*